United States Patent
Alchemy et al.

(10) Patent No.: US 11,854,700 B1
(45) Date of Patent: Dec. 26, 2023

(54) METHOD OF AND SYSTEM FOR DETERMINING A HIGHLY ACCURATE AND OBJECTIVE MAXIMUM MEDICAL IMPROVEMENT STATUS AND DATING ASSIGNMENT

(71) Applicant: Alchemy Logic Systems Inc., Santa Rosa, CA (US)

(72) Inventors: John William Alchemy, Santa Rosa, CA (US); Jerry Lee Artz, St. Paul, MN (US); Daniel Ryan Penn, Santa Rosa, CA (US)

(73) Assignee: Alchemy Logic Systems, Inc., Santa Rosa, CA (US)

( * ) Notice: Subject to any disclaimer, the term of this patent is extended or adjusted under 35 U.S.C. 154(b) by 0 days.

(21) Appl. No.: 15/833,541

(22) Filed: Dec. 6, 2017

Related U.S. Application Data

(60) Provisional application No. 62/430,847, filed on Dec. 6, 2016.

(51) Int. Cl.
  *G16H 50/30* (2018.01)
  *G16H 50/20* (2018.01)
  *G16H 10/60* (2018.01)

(52) U.S. Cl.
  CPC .............. *G16H 50/30* (2018.01); *G16H 10/60* (2018.01); *G16H 50/20* (2018.01)

(58) Field of Classification Search
  CPC ......... G16H 50/30; G16H 10/60; G16H 50/20
  See application file for complete search history.

(56) References Cited

U.S. PATENT DOCUMENTS

| | | |
|---|---|---|
| 4,916,611 A | 4/1990 | Doyle, Jr. et al. |
| 4,987,538 A | 1/1991 | Johnson et al. |
| 5,182,705 A | 1/1993 | Barr et al. |
| 5,367,675 A | 11/1994 | Cheng et al. |
| 5,517,405 A | 5/1996 | McAndrew et al. |
| 5,544,044 A | 8/1996 | Leatherman |
| 5,613,072 A | 3/1997 | Hammond et al. |
| 5,778,345 A | 7/1998 | McCartney |
| 5,911,132 A | 6/1999 | Sloane |

(Continued)

FOREIGN PATENT DOCUMENTS

| | | |
|---|---|---|
| CA | 2707207 A1 | 6/2009 |
| WO | WO2008006117 A2 | 1/2008 |
| WO | 2018224937 A1 | 12/2018 |

OTHER PUBLICATIONS

Rondinelli, Robert D., Guides to the Evaluation of Permanent Impairment, 2008 Sixth Edition, American Medical Association.

(Continued)

*Primary Examiner* — Scott Luan
(74) *Attorney, Agent, or Firm* — Haverstock & Owens a Law Corporation

(57) ABSTRACT

A method of and system for the determination of MMI to assist in injury and exposure claim adjudication by assisting stakeholders access to a metric system analysis based on an objective claim data set. The method and system utilizes a recovery score index for determining whether the individual is medically stable and one or more recovery phase classifications for determining that available treatment has been provided to the individual. Based on these metrics, the present invention is able to determine a highly accurate and objective maximum medical improvement status and dating assignment.

22 Claims, 2 Drawing Sheets

(56) References Cited

U.S. PATENT DOCUMENTS

| | | | |
|---|---|---|---|
| 6,003,007 A | 12/1999 | DiRienzo | |
| 6,065,000 A | 5/2000 | Jensen | |
| 6,604,080 B1 | 8/2003 | Kern | |
| 6,810,391 B1 | 10/2004 | Birkhoelzer et al. | |
| 6,865,581 B1 | 3/2005 | Cloninger, Jr. | |
| 6,954,730 B2 | 10/2005 | Lau et al. | |
| 6,957,227 B2 | 10/2005 | Fogel | |
| 7,337,121 B1 | 2/2008 | Beinat | |
| 7,401,056 B2 | 7/2008 | Kam | |
| 7,440,904 B2 | 10/2008 | Hasan et al. | |
| 7,475,020 B2 | 1/2009 | Hasan et al. | |
| 7,509,264 B2 | 3/2009 | Hasan et al. | |
| 7,630,911 B2 | 12/2009 | Kay | |
| 7,630,913 B2 | 12/2009 | Kay | |
| 7,707,046 B2 | 4/2010 | Kay | |
| 7,707,047 B2 | 4/2010 | Hasan et al. | |
| 7,778,849 B1 | 8/2010 | Hutton | |
| 7,813,944 B1 | 10/2010 | Luk | |
| 7,870,011 B2 | 1/2011 | Kay | |
| 7,904,309 B2 | 3/2011 | Malone | |
| 7,930,190 B1 | 4/2011 | Milanovich | |
| 7,949,550 B2 | 5/2011 | Kay | |
| 7,970,865 B2 | 6/2011 | DeCesare et al. | |
| 8,019,624 B2 | 9/2011 | Malone | |
| 8,041,585 B1 | 10/2011 | Binns et al. | |
| 8,065,163 B2 | 11/2011 | Morita et al. | |
| 8,069,066 B2 | 11/2011 | Stevens et al. | |
| 8,185,410 B2 | 5/2012 | Brigham | |
| 8,301,575 B2 | 10/2012 | Bonnet et al. | |
| 8,346,573 B2 | 1/2013 | Glimp et al. | |
| 8,489,413 B1 | 7/2013 | Larson et al. | |
| 8,489,424 B2 | 7/2013 | Hasan et al. | |
| 8,510,134 B1 | 8/2013 | Sweat et al. | |
| 8,527,303 B2 | 9/2013 | Kay | |
| 8,615,409 B1 | 12/2013 | McKown | |
| 8,630,878 B1 | 1/2014 | Kravets et al. | |
| 8,725,524 B2 | 5/2014 | Fano | |
| 8,725,538 B2 | 5/2014 | Kay | |
| 8,751,252 B2 | 6/2014 | Chamberlain | |
| 8,751,263 B1 | 6/2014 | Cave et al. | |
| 8,751,266 B2 | 6/2014 | Stang | |
| 8,775,216 B1 | 7/2014 | Amick et al. | |
| 8,864,663 B1 | 10/2014 | Kahn et al. | |
| 8,868,768 B2 | 10/2014 | Sokoryansky | |
| 8,888,697 B2 | 11/2014 | Bowman et al. | |
| 8,900,141 B2 | 12/2014 | Smith et al. | |
| 8,910,278 B2 | 12/2014 | Davne et al. | |
| 8,930,225 B2 | 1/2015 | Morris | |
| 8,959,027 B2 | 1/2015 | Kusens | |
| 8,954,339 B2 | 2/2015 | Schaffer | |
| 9,002,719 B2 | 4/2015 | Tofte | |
| 9,015,055 B2 | 4/2015 | Tirinato et al. | |
| 9,020,828 B2 | 4/2015 | Heidenreich | |
| 9,229,917 B2 | 1/2016 | Larcheveque | |
| 9,710,600 B1 | 7/2017 | Dunleavy | |
| 2001/0027331 A1 | 10/2001 | Thompson | |
| 2001/0044735 A1 | 11/2001 | Colburn | |
| 2001/0053984 A1 | 12/2001 | Joyce | |
| 2002/0069089 A1 | 6/2002 | Arkin | |
| 2002/0077849 A1 | 6/2002 | Baruch | |
| 2004/0044546 A1 | 3/2004 | Moore | |
| 2005/0060184 A1 | 3/2005 | Wahlbin | |
| 2005/0177403 A1 | 8/2005 | Johnson | |
| 2005/0256744 A1 | 11/2005 | Rohde | |
| 2006/0161456 A1 | 7/2006 | Baker | |
| 2006/0287879 A1 | 12/2006 | Malone | |
| 2007/0118406 A1 | 5/2007 | Killin | |
| 2007/0250352 A1 | 10/2007 | Tawil | |
| 2008/0046297 A1 | 2/2008 | Shafer | |
| 2008/0133297 A1 | 6/2008 | Schmotzer | |
| 2008/0154672 A1 | 6/2008 | Skedsvold | |
| 2008/0183497 A1 | 7/2008 | Soon | |
| 2009/0099875 A1 | 4/2009 | Koeniq | |
| 2010/0042435 A1 | 2/2010 | Kay | |
| 2010/0106520 A1 | 4/2010 | Kay | |
| 2010/0106526 A1 | 4/2010 | Kay | |
| 2010/0114609 A1 | 5/2010 | Duffy, Jr. et al. | |
| 2010/0217624 A1 | 8/2010 | Kay | |
| 2010/0240963 A1 | 9/2010 | Brighman | |
| 2011/0077980 A1 | 3/2011 | Kay | |
| 2011/0077981 A1 | 3/2011 | Kay | |
| 2011/0145012 A1 | 6/2011 | Nightingale | |
| 2011/0161115 A1 | 6/2011 | Hampton | |
| 2011/0257919 A1 | 10/2011 | Reiner | |
| 2011/0257993 A1 | 10/2011 | Shahani | |
| 2011/0313785 A1 | 12/2011 | Lash | |
| 2011/0313912 A1 | 12/2011 | Teutsch | |
| 2012/0022884 A1 | 1/2012 | Chillemi | |
| 2012/0102026 A1 | 4/2012 | Fortune | |
| 2012/0130751 A1 | 5/2012 | McHugh | |
| 2012/0232924 A1 | 9/2012 | Bingham | |
| 2012/0245973 A1 | 9/2012 | Pandya | |
| 2012/0278095 A1 | 11/2012 | Homchowdhury | |
| 2012/0284052 A1 | 11/2012 | Saukas | |
| 2013/0024214 A1 | 1/2013 | Schoen et al. | |
| 2013/0132122 A1 | 5/2013 | Walsh | |
| 2014/0052465 A1 | 2/2014 | Madan | |
| 2014/0058763 A1 | 2/2014 | Zizzamia | |
| 2014/0073486 A1 | 3/2014 | Ahmed | |
| 2014/0136216 A1 | 5/2014 | Beebe | |
| 2014/0172439 A1 | 6/2014 | Conway et al. | |
| 2014/0201213 A1 | 7/2014 | Jackson | |
| 2014/0249850 A1 | 9/2014 | Woodson | |
| 2014/0278479 A1 | 9/2014 | Wang et al. | |
| 2014/0278830 A1 | 9/2014 | Gagne | |
| 2014/0303993 A1 | 10/2014 | Florian | |
| 2015/0019234 A1 | 1/2015 | Cooper | |
| 2015/0221057 A1 | 8/2015 | Raheja et al. | |
| 2015/0235334 A1 | 8/2015 | Wang et al. | |
| 2015/0242585 A1 | 8/2015 | Spiegel | |
| 2015/0278462 A1 | 10/2015 | Smoley | |
| 2015/0286792 A1 | 10/2015 | Gardner | |
| 2015/0324523 A1 | 11/2015 | Parthasarathy et al. | |
| 2016/0063197 A1 | 3/2016 | Kumetz | |
| 2016/0125544 A1 | 5/2016 | Edwards | |
| 2016/0283676 A1 | 9/2016 | Lyon et al. | |
| 2016/0292371 A1 | 10/2016 | Alhimiri | |
| 2017/0140489 A1 | 5/2017 | Ziobro | |
| 2017/0154374 A1 | 6/2017 | Iglesias | |
| 2017/0177810 A1 | 6/2017 | Fulton | |
| 2017/0228517 A1 | 8/2017 | Saliman | |
| 2017/0255754 A1 | 9/2017 | Allen | |
| 2017/0316424 A1 | 11/2017 | Messana | |
| 2017/0352105 A1 | 12/2017 | Billings | |
| 2018/0025334 A1 | 1/2018 | Pourfallah | |
| 2018/0279919 A1 | 10/2018 | Bansbach | |
| 2019/0065686 A1 | 2/2019 | Crane | |
| 2020/0126645 A1 | 4/2020 | Robbins | |
| 2020/0279622 A1 | 9/2020 | Heywood | |
| 2020/0286600 A1 | 9/2020 | De Brouwer | |

OTHER PUBLICATIONS

Cocchiarella, Linda and Andersson, Gunnar B. J., Guides to the Evaluation of Permanent Impairment, 2001 Fifth Edition, American Medical Association.

Park, Y., Butler, R. J. (2000). Permanant Partial Disability Awards and Wage Los. Journal of Risk and Insurance, 67(3), 331. Retrieved from https"//dialog.proquest.com/professional/docview/769439682, Year 2000, 18 pages.

In B. Pfaffenberger, Webster's new World&Trade; Computer Dictionary(10th ed). Houghton Mifflin Harcourt, Credo reference:https://search.credoreference.com/content/entry/webster.com/database(year 2003).

In B. Pfaffenberger, Webster's new World&Trade; Computer Dictionary(10th ed). Houghtpon Mifflin Harcourt, Credo reference:https://search.credoreference.com/content/entry/webster.com/database(year 2003).

"Physician's Guide to Medical Practice in the California Worker's Compensation System", 2016, State of California Department of Industrial Relations Division of Worker's Compensation, 4th ed., all pages. (Year 2016).

(56) References Cited

OTHER PUBLICATIONS

American College of Occupational and Environmental Medicine, Occupational Medicine Practice Guidelines, 2004, Second Edition, OEM Press, Beverly Farms, MA.

CA Medical Treatment Utilization Schedule, Proposed Chronic Pain Medical Treatment Guidelines, Jun. 2008, 83 pages.

Hakkinen, Arja, et al. "Muscle strength, pain, and disease activity explain individual subdimensions of the Health Assessment Questionaire disability index, especially in women with rheumatoid arthritis." Annals of the rheumatic diseases 65.1 (2006): 30-34. (Year: 2006).

"CA DWC Releases 4th Edition of Physician's Guide to Medical Practice in CA WC", Apr. 5, 2016, workcompwire.com, 7 pages.

Programming languages. (2004). In W. S. Bainbridge (Ed)., Berkshire encylopedia of human-computer interaction. Berkshire Publishing Group. Credo Reference: https://search.credoreference.com/content/entry/berkencyhci/programming_languages/0? institutionid=743 (Year: 2004), 5 pages.

Ammendolia C. Cassidy D., Steensta I, et al. Designing a Workplace Return-to Work Program for Occupational Low Back Pain: an intervention mapping approach. BMC Musculoskelet Disord. 2009; 10:65. Published Jun. 9, 2009. doi: 10.1186/1471-2474-10-65 (Year; 2009). 10 pages.

Wasiak, Radoslaw, et al. "Measuring Return To Work." Journal of Occupational Rehabilitation 17.4 (2007): 766-781. (Year: 2007). 16 pages.

METHOD OF AND SYSTEM FOR DETERMINING A HIGHLY ACCURATE AND OBJECTIVE MAXIMUM MEDICAL IMPROVEMENT STATUS AND DATING ASSIGNMENT

Related Applications

This Patent Application claims priority under 35 U.S.C. 119(e) of the co-pending U.S. provisional patent application, Application No. 62/430,847, filed on Dec. 6, 2016, and entitled "METHOD TO DETERMINE HIGHLY ACCURATE OBJECTIVE MAXIMAL MEDICAL IMPROVEMENT (MMI) STATUS AND DATING ASSIGNMENT," which is hereby incorporated in its entirety by reference.

Field of the Invention

The present invention is generally directed to the determining Maximum Medical Improvement (MMI) for an injury. More specifically, the present invention is directed to a method of and system for determining MMI status and dating assignment.

BACKGROUND OF THE INVENTION

A current flaw in the determination of MMI can be a medical provider's subjective interpretation of medical recovery which can result in claim adjudication delay, error, and excessive cost of medical treatments all of which no longer contribute to an active individual's well being and functional advancement. Determining and assigning a MMI date is a foundation of the injury recovery process. It is the MMI date which determines that no further medical improvement is expected and allows adjudication of the claim to proceed. Successful adjudication means that a permanent impairment is assigned to the worker, benefits can be provided, permanent functional limitations are created and eligibility for vocational retraining can be addressed.

SUMMARY OF THE INVENTION

The present invention is directed to a method of and system for the determination of MMI to assist in injury and exposure claim adjudication by assisting stakeholders access to a metric system analysis based on an objective claim data set. The method and system utilizes a recovery score index for determining whether the individual is medically stable and one or more recovery phase classifications for determining that available treatment has been provided to the individual. Based on these metrics, the present invention is able to determine a highly accurate and objective maximum medical improvement status and dating assignment.

In one aspect, a method of determining maximum medical improvement and dating assignment comprises determining a recovery score index for an injured individual at $T_0$, if the recovery score index is $\geq 1$, then determine a recovery phase classification at $T_0$, determining a recovery score index for an injured individual at $T_1$, if the recovery score index is $\geq 1$, then determining a recovery phase classification at $T_1$, calculating a recovery score index delta based on the recovery score index at $T_1$ and the recovery score index at $T_0$, calculating a recovery velocity based on the recovery score index delta and time between $T_0$ and $T_1$, and based on the recovery velocity and the recovery phase calculation calculating the date of maximum medical improvement for the injured individual. In some embodiments, determining the recovery score index comprises surveying one or more biologic and functional metrics of the injured individual. In some embodiments, the time between $T_0$ and $T_1$ is dependent upon one or more administrative rule sets for the injury. In some embodiments, determining the recovery phase classification comprises determining whether available treatment for the injury has been exhausted. In some embodiments, the available treatment options comprise one or more of medications, therapies, diagnostic testing, and specialty consulting. In further embodiments, available treatment is classified according to four stages. In some embodiments, if the recovery velocity is one of positive and neutral and available treatment has been exhausted then the maximum medical improvement date is $T_0$. In further embodiments, if the recovery velocity is one of positive and neutral and available treatment has not been exhausted then treatment is continued according to the appropriate administrative rule sets and recovery phase classification is determined at $T_N$. In some embodiments, the recovery velocity is negative. In some of these embodiments, if the available treatment has been exhausted then the maximum medical improvement date is $T_0$. In further embodiments, if the recovery velocity is $\leq -0.167$ RSID/week (using the California rule set in this example which requires a sampling no less than every 45 days) then treatment is continued according to the appropriate administrative rule sets and recovery phase classification is determined at $T_N$. In still further embodiments, if the recovery velocity is $\geq -0.167$ RSID/week and available treatment has not been exhausted, then treatment is continued according to the appropriate administrative rule sets and recovery phase classification is determined at $T_N$.

In another aspect, a method of determining a rate of recovery for an injury comprises determining a recovery score index for an injured individual at $T_0$, determining a recovery score index for the injured individual at $T_N$, and based on the recovery score index at $T_N$ and the recovery score index at $T_0$ and the time between $T_0$ and $T_N$ calculating a rate of recovery for the injury. In some embodiments, determining the recovery score index comprises surveying one or more biologic and functional metrics of the injured individual. In some embodiments, the time between $T_0$ and $T_N$ is dependent upon one or more administrative rule sets for the injury. In some embodiments, the rate of recovery for the injury is one of positive, neutral, and negative.

In a further aspect, a system for determining a maximum medical improvement and dating assignment for an injury comprises a recovery score index input, a recovery phase classification input, and a maximum medical improvement calculator coupled to the recovery score index input and the recovery phase classification input, wherein the maximum medical improvement calculator is configured to output a maximum medical improvement date based on one or more information metrics received from the recovery score index input and the recovery phase classification input. In some embodiments, the recovery score index input is based on a scale from 1 to 10. In some embodiments, the recovery score index input comprises information from one or more biologic and functional metrics of the injured individual. In some embodiments, the recovery score index input is configured to receive a plurality of inputs at time $T_0$ and time $T_1$. In some of these embodiments, the time between $T_0$ and $T_1$ is dependent upon one or more administrative rule sets for the injury. In some embodiments, the recovery phase classification input comprises one or more available treatments for injury. In some embodiments, the available treatments comprise one or more of medications, therapies, diagnostic testing, and specialty consulting. In further embodiments, available treatment options are classified according to four stages. In some embodiments, the maximum medical improvement calculator determines whether the available treatment options have been exhausted.

DETAILED DESCRIPTION OF THE EMBODIMENTS

Figure 1:
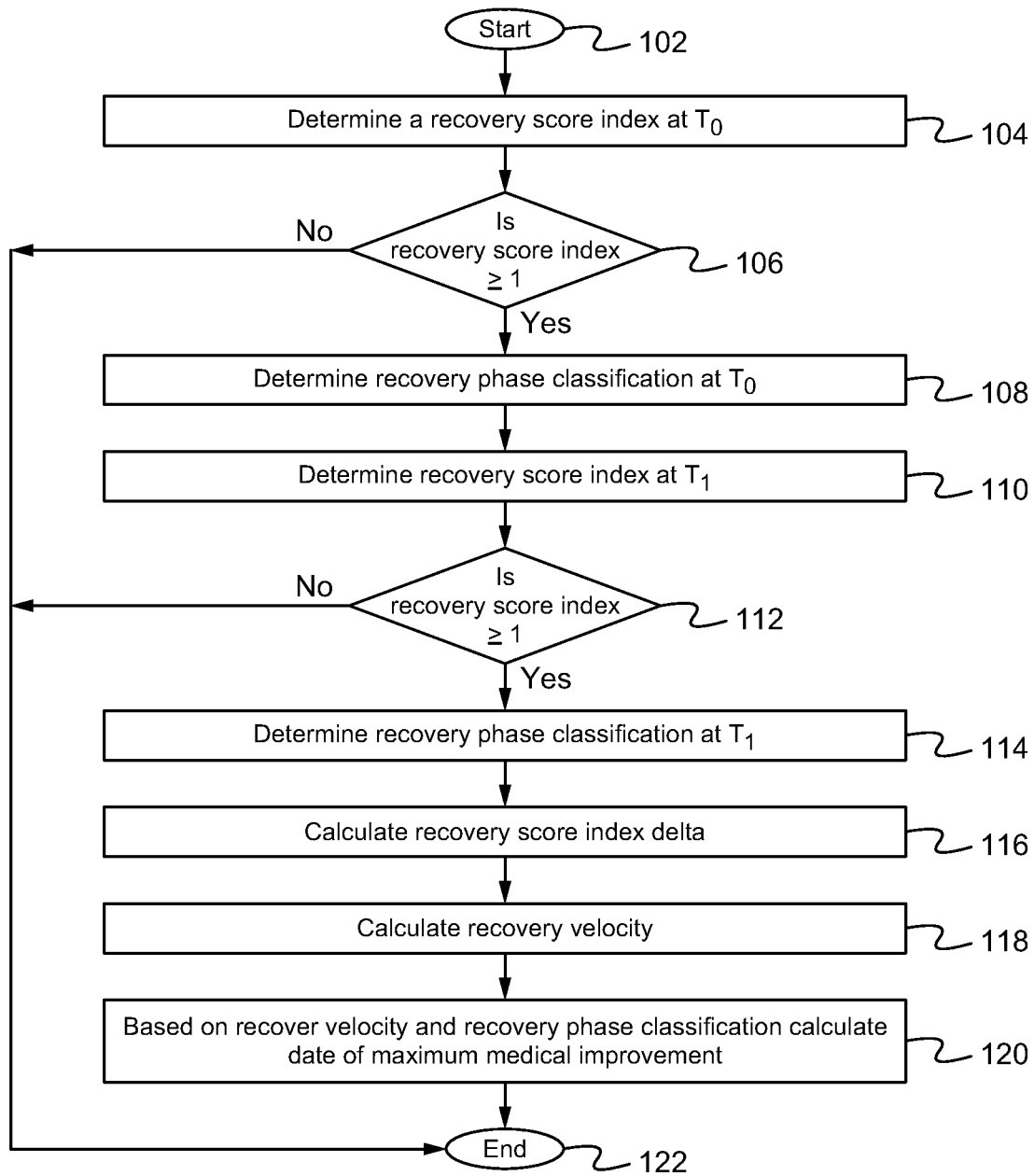
FIG. 1 illustrates a method of determining a MMI and date of MMI in accordance with some embodiments.

Embodiments of the invention are directed to a method of and system for the determination of MMI to assist in injury and exposure claim adjudication by assisting stakeholders access to a metric system analysis based on an objective claim data set. The invention includes but is not limited to administrative rule sets (ARS), such as those described in U.S. patent application Ser. No. 14/996,067 to Alchemy et al., (hereinafter "the '067 Application"), which is hereby incorporated by reference, and for worker's compensation, personal injury and social security claims. The MMI date is a critical date in a claim that signals that there is no further anticipated improvement of the injury. As described by the American Medical Association (AMA) Guide, "an impairment is considered permanent when it has reached Maximum Medical Improvement (MMI), meaning that it is well stabilized and unlikely to change substantially within the next year with or without medical treatment." [AMA Guide, $5^{th}$ Ed., p. 2] The MMI date next allows a determination of a Permanent Impairment Whole Person Value, which adjudicates financial and medical benefits, including further access to care and vocational consideration for the ability of an injured individual to return to employment. The present invention describes key aspects for obtaining critical data measurements and determining an analytical matrix system for the systematic organization of data, including a completeness of a data set with bounded value results.

Reference will now be made in detail to implementations of a method of and system for determining a highly accurate and objective MMI status and dating assignment for an injury as illustrated in the accompanying drawings. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The present invention describes a determination of MMI for an individual beginning with an assessment of the individual and an assessment of the available treatment completed by the individual. A Recovery Score Index (RSI) for an initial visit at $T_0$ (RSI $T_0$) of the individual is a representative value of recovery based on a multi-factor survey of the individual, including subjective and biologic measurements and functional metrics. Historic treatment interventions such as medications, therapies, diagnostic testing, and specialty consulting are placed into a Recovery Phase Classification (RPC) stage. In a second visit for the injured individual at $T_1$, a second RSI $T_1$ is compared to RSI $T_0$. The difference between RSI $T_1$ and RSI $T_0$ is the Recovery Score Index Delta (RSID) for the injured individual. The time between RSI $T_1$ and RSI $T_0$ can be used as a denominator for the RSID to determine the Recovery Velocity (RV). The RV is either positive, negative, or unchanging indicating the rate and direction of recovery. Additionally, the RV value can be standardized for treatment time according to the correct ARS. For example, in California Worker's Compensation cases, an injured individual is required to be seen no less than every 45 days. For any time interval shorter than that defined by the ARS, an extrapolation can be performed to identify the injured individual's trajectory for the period of time defined by the ARS. The present invention allows stakeholder's an objective insight into the individual's recovery status including recovery magnitude (RSI), recovery trend (RSID), recovery velocity (RV) and a verifiable date of MMI, past, present, or future.

The system substantially eliminates the subjectivity of the evaluator. Depending upon the nature of the injury the system directs the evaluator to measure and input a predetermined set of factors. Based upon these factors the system, and not the evaluator, assigns the RSI. Each visit to the evaluator results in a new updated RSI based on the same set of factors. In this way, the evaluator cannot introduce 'human error' into the determination of MMI in light of their predilections, current circumstances or mood. Rather the system receives the input it requires from the evaluator to generate the appropriate and accurate RSI. The system stores the series of RSI values and generates an accurate MMI.

The present invention has two principle concepts 1) determining whether an individual is medically stable such that there has been no significant change in the injury for a defined period of time and 2) determining that all available treatment has been provided to the injured individual.

Medical stability is determined by a percentage change in the slope of the RV over time (RV). Two metrics are used to determine active recovery. The first metric is RV, such as described above. This metric has two sub-requirements for validating whether active recovery is present for the injured individual. The first sub-requirement i) is the delta must be a change of 10%. The 10% change must be a 10% of the RSI scale and not 10% of the RSI value. The second sub-requirement ii) is the time value between $T_0$ and $T_1$. As described above, if the time value between $T_0$ and $T_1$ is not as prescribed by the appropriate ARS, then an extrapolation can be performed to determine an actual or true RV value. A RV ≥−0.167 RSID/week indicates active clinical recovery has been completed and that the injured individual is medically stable.

The verification that available treatment has been delivered is determined according to the RPC, such as described above. The status of available treatment is classified into four stages I-IV, where Ia=conservative care active/ongoing; Ib=conservative care complete, IIa=diagnostic testing/consultation active/ongoing; IIb=diagnostic testing/consultation complete, IIIa=interventional active; IIIb=interventional complete; and all available treatment complete IV; where IIIb=IV). A score of IIIa and lower indicates all available treatment has not been completed. A score of IIIb and above indicates all available treatment has been delivered to the injured individual.

When the injured worker is medically stable and has completed available treatment, then the individual has achieved MMI. The MMI date can be past, present and future. Using rigorous scalar determination and statistical methods, an objective consistent result can be obtained to determine recovery movement, recovery directions, and recovery rate and/or velocity.

FIG. 1 illustrates a method of determining a MMI and date of MMI in accordance with the present invention. The method begins in the step 102. In the step 104, a RSI for an initial visit RSI $T_0$ is determined. As described above, the RSI is a representative value of recovery based on a multi-factor survey of the individual. For example, in some embodiments the intake elements comprise a pain visual analog scale, frequency of symptoms, activities of daily living (ADLs), present work status, biological measurements, for example range of motion, strength, and muscle girth, sensory measurements, diagnostic testing such as x-ray and electro diagnostic nerve testing, and functional work limitations. As described above, the RSI value is expressed as a value between 0 and 10. A score of 0 represents a full and complete return to function with no pain, no biologic loss or work function loss. This is a best restorative outcome. A score of 10 is the worst possible outcome.

In the step 106, if the RSI is 0, this indicates that the injured individual is fully recovered and the date of MMI is verified at RSI $T_0$. The method ends at the step 122. If the RSI $T_0$ is ≥1, then the method proceeds to the step 108.

In the step 108, the RPC is determined at $T_0$. At $T_0$, the treatment received by the injured worker to date is classified to determine whether all available treatment has been exhausted. This assessment is determined by the appropriate ARS(s) for the injured worker and the claim. For example, for Worker's Compensation cases in California, available treatment is dependent on the Medical Treatment Utilization Schedule (MTUS), American College of Occupational and Environmental Medicine (ACOEM) $2^{nd}$ Edition, and the Official Disability Guidelines (ODG).

As described above, available treatment is classified into four stages I-IV, where Ia=conservative care active/ongoing; Ib=conservative care complete, IIa=diagnostic testing/consultation active/ongoing; IIb=diagnostic testing/consultation complete, IIIa=interventional active; IIIb=interventional complete; and all available treatment complete IV; where IIIb=IV). A score of IIIa and lower indicates all available treatment has not been completed. A score of IIIb and above indicates all available treatment has been delivered to the injured individual. If the score is <IIIb, then further treatment is recommended. If the score is ≥IIIb, then treatment is determined complete.

In the step 110, a RSI is determined for a next visit at $T_1$. In the step 112, if a score of 0 indicates full recovery for the individual and the method ends in the step 122. If at step 112, the RSI $T_1$ is ≥1, then the method proceeds to the step 114.

In the step 114, the RPC at $T_1$ is determined. If the score is <IIIb, then further treatment is recommended. If the score is ≥IIIb, then treatment is determined complete.

In the step 116, the RSID is determined for the injured individual. As described above, the RSID is the difference between RSI $T_1$ and RSI $T_0$. The RV is determined based on the RSID in the step 118. As described above, the RV is the RSID divided by the time interval between RSI $T_1$ and RSI $T_0$. In some embodiments, the RV value is standardized for time according to the correct ARS. Based on the recovery velocity and the recovery phase classification, a date of maximum medical improvement is calculated in the step 120.

As described above, the RV can be positive, negative, or unchanging indicating the rate and direction of recovery. A positive RV indicates a worsening of the injury and a trending of the RSI to 10. A neutral RV indicates a static and unchanging injury condition. A negative RV indicates that the injury is improving and a trending of the RSI to 0.

If RV is positive and RPC is ≤IIIb, then available treatment is continued and RPC can be re-checked according to the ARS schedule for the injury. If RV is positive and RPC is ≥IIIb, then treatment is determined complete and the MMI date is verified at $T_0$.

If RV is neutral and RPC is ≤IIIb, then available treatment is continued and RPC can be re-checked according to the ARS schedule for the injury. If the RV is neutral and RPC is ≥IIIb, then treatment is determined complete and the MMI date is verified at $T_0$.

If the RV is negative and ≤−0.167 RSID/week, then the RV is rechecked in the time interval between RSI $T_1$ and RSI $T_0$, available treatment is continued and RPC can be re-checked according to the ARS schedule for the injury.

If RV is ≥−0.167 and RPC is <IIIb or less, available treatment is continued and RPC can be re-checked according to the ARS schedule for the injury. If RV is ≥−0.167 and RPC is ≥IIIb, then treatment is determined complete and the MMI is verified at $T_0$.

The method ends in step 122.

Examples of the Method Such as Described Above

For examples (where T=0 is the initial visit data available; T=1 is a visit subsequent to T=0; T=2 is a future date subsequent to T1; RSI is bounded as a whole number between 0 and 10. x=any RSI defined value at T=0, and is a whole integer, and y=any RSI defined value at T=1 and is a whole integer; and the recovery velocity is given; n/a means not applicable.)

Example 1—A complete recovery at MMI at T=0 visit (single visit analysis).
RSI Score T=0: x; where x is 0.
RSI Score T=: n/a
RPC Score: n/a
RSID: n/a
RV (6 wk sampling): n/a
MMI Determination: MMI; T=0
A complete recovery is documented at T
Example 2—A complete recovery at MMI at T=1.
RSI Score T=0: x; where x is any number other than 0.
RSI Score T=1: y=0.
RPC Score: n/a
RSID: improving (−slope e.g. <−1)
RV (6 wk sampling): n/a
MMI Determination: MMI; T=1.
A complete recovery is documented at T
Example 3—An active (improving recovery); RV remains active; treatment remains available. not MMI.
RSI Score T=0: x; where x is any number other than 0, 1 or 2.
RSI Score T=1: y; where y is a number less than x but not 0.
RPC Score: <IIIb
RSID: improving (−slope e.g. <−1)
RV (6 wk sampling): required.

MMI Determination: Not MMI; MMI projected arrested by RPC not complete.

An active improving trend of at least 10% variance is documented over a 6 wk interval according to the California ARS used in this example.

Example 4—A static recovery; RV static; treatment remains available; not MMI.
  RSI Score T=0: x; where x is any number other than 0.
  RSI Score T=1: y; where y is a number=x.
  RPC Score: <IIIb
  RSID: static (slope=0 or <1)
  RV (6 wk sampling actual or extrapolated): required.
  MMI Determination: Not MMI; MMI projected date not delivered (arrested by RPC not complete).
  A static recovery with more available treatment.

Example 5—An active (improving recovery); RV remains active; treatment complete; not MMI.
  RSI Score T=0: x; where x is any number other than 0, 1 or 2.
  RSI Score T=1: y; where y is a number less than x but not 0.
  RPC Score: IIIb or IV
  RSID: improving (-slope e.g. <-1)
  RV (6 wk sampling): required.
  MMI Determination: Not MMI present or past, MMI projected date is delivered.
  Complete treatment, active (improving) recovery. MMI may be extrapolated for a projected date in the future (T=2).

Example 6—An active (worsening) recovery; RV remains active; treatment complete. MMI.
  RSI Score T=0: x; where x is any number other than 0 and less than 9.
  RSI Score T=1: y; where y is any number greater than x.
  RPC Score: IIIb or IV
  RSID: worsening (+slope e.g.. >1)
  RV (6 wk sampling): required.
  MMI Determination: MMI; date is T=0.
  Complete treatment, active worsening recovery. MMI date is T=0.

Example 7—A static recovery; RV static; treatment complete; MMI.
  RSI Score T=0: x; where x is any number other than 0.
  RSI Score T=1: y; where y is a number=x.
  RPC Score: IIIb or IV
  RSID: static (slope=0 or <1)
  RV (6 wk sampling): required.
  MMI Determination: MMI; date is T=0.
  Complete treatment, static recovery. MMI date is retroactive to T=0.

Example 8—A worsening (not improving) recovery; RV positive; treatment remains available; not MMI.
  RSI Score T=0: x; where x is any number other than 0 and less than 9.
  RSI Score T=1: y; where y is any number greater than x.
  RPC Score: <IIIb
  RSID: worsening (+slope e.g. >1)
  RV (6 wk sampling): required.
  MMI Determination: Not MMI; MMI projected date not delivered (arrested by RPC not complete).
  Complete treatment, active worsening recovery. MMI date is retroactive to T=0.

Figure 2:
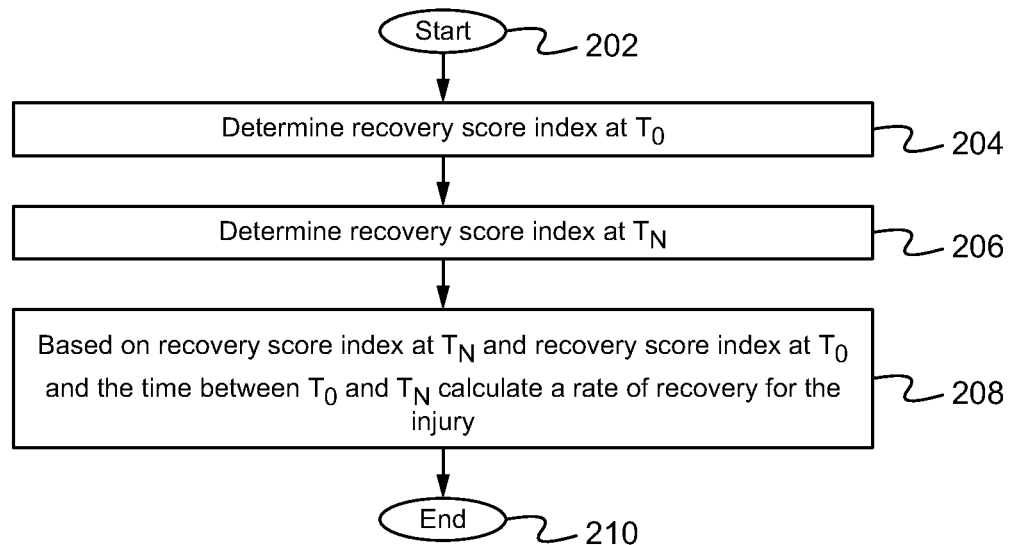
FIG. 2 illustrates a method of determining a recovery rate time line for an injury in accordance with some embodiments.

FIG. 2 illustrates a method of determining a recovery rate time line for an injury in accordance with some embodiments of the present invention. The method begins in the step 202. In the step 204, a RSI for an injured individual is determined at $T_0$. As described above, in some embodiments, determining the RSI comprises surveying one or more biologic and functional metrics of the injured individual. In the step 206, a RSI for the injured individual is determined at time $T_N$. In some embodiments, the time between $T_0$ and $T_N$ is dependent upon one or more ARSs for the injury. Then, in the step 208, based on the RSI at $T_N$ and the RSI at $T_0$ and the time between $T_0$ and $T_N$ a rate of recovery for the injury is calculated. In some embodiments, the rate of recovery for the injury is one of positive, neutral, and negative. The method ends in the step 210.

Figure 3:
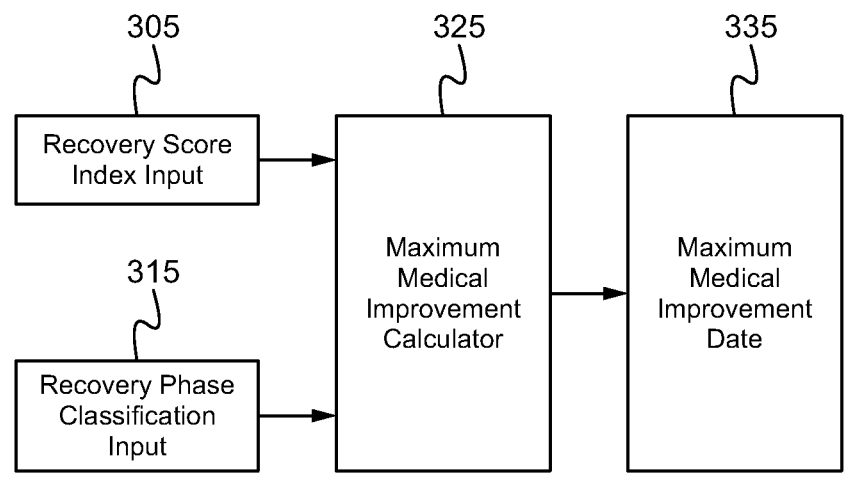
FIG. 3 illustrates a system for determining a maximum medical improvement and dating assignment for an injury, in accordance with some embodiments.

FIG. 3 illustrates a system for determining a maximum medical improvement and dating assignment for an injury. The system comprises a recovery score index input 305, a recovery phase classification input 315 and a maximum medical improvement calculator 325. As shown within FIG. 3, the maximum medical improvement calculator 325 is coupled to the recovery score index input 305 and the recovery phase classification input 315. In some embodiments, the maximum medical improvement calculator 325 is configured to output a maximum medical improvement date 335 based on one or more information metrics received from the recovery score index input 305 and the recovery phase classification input 315.

In some embodiments, the recovery score index input is based on a scale from 1 to 10. In some embodiments, the recovery score index input comprises information from one or more biologic and functional metrics of the injured individual. The recovery score index input 305 is configured to receive a plurality of inputs at time $T_0$ and time $T_1$. However, the recovery score index input 305 can receive any appropriate number of inputs based on the injury. In some embodiments, the time between $T_0$ and $T_1$ is dependent upon one or more administrative rule sets for the injury.

In some embodiments, the recovery phase classification input comprises one or more available treatments for injury. The available treatments can comprise one or more of medications, therapies, diagnostic testing, and specialty consulting. In some embodiments, the available treatment options are classified according to four stages. In some embodiments, the maximum medical improvement calculator determines whether the available treatment options have been exhausted.

In operation, the method of and system for determining a highly accurate and objective MMI status and dating assignment for an injury addresses the current flaws in a medical provider's subjective MMI interpretation of medical recovery. Consequently, the present invention reduces delay, error, and costs. The present invention provides three distinct components; data inquiry, data computation, and data trend analysis and results.

Particularly, the present invention allows medical and legal industries to utilize a fact driven and systematic approach for determining MMI. Additionally, the present invention allows stakeholders to objectively identify MMI using permanent impairment measures including but not limited to, fatigue and pain, biologic measurements, anatomic loss, functional loss, ADLs, and work functional limitations.

The present invention then allows stakeholders to understand what treatment has been undertaken, results of prior treatment and therefore determine the next treatment and/or diagnostic steps based on further available treatments. This enables a specific calendar date of expected and/or actual MMI based on the variables unique to the claim to be delivered. In some embodiments, this information can be delivered using a graphic or numeric dashboard for a user and thus understand a recovery event in the context of a similar injury and/or circumstance.

As such the method of and system for determining a highly accurate and objective MMI status and dating assignment for an injury such as described herein has many advantages.

The present invention has been described in terms of specific embodiments incorporating details to facilitate the understanding of the principles of construction and operation of the invention. As such, references, herein, to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A method of optimizing a determination of maximum medical improvement and dating assignment, the method comprising:

performing a multi-factor survey of an injured individual at $T_0$ for an injury sustained by the injured individual to obtain $T_0$ measurements associated with a predetermined set of factors, wherein the $T_0$ measurements include biologic measurements and functional metrics of the injured individual at $T_0$, wherein performing the multi-factor survey at $T_0$ comprises at least using one or more diagnostic testing equipments on the injured individual to obtain at least a portion of the biologic measurements and functional metrics of the injured individual at $T_0$;

determining, by a computing device, a recovery score index for the injured individual at $T_0$ according to a predetermined technique reducing $T_0$ scalar values associated with the predetermined set of factors to a single representative value indicative of the injured individual's recovery status at $T_0$, wherein the $T_0$ scalar values correspond with at least a portion of the $T_0$ measurements obtained according to one or more administrative rule sets, wherein the predetermined technique includes applying one or more statistical methods to one or more sets of scalar values that correspond with measurements obtained according to the one or more administrative rule sets;

if the recovery score index at $T_0$ is 1, then determining, by the computing device, a recovery phase classification at $T_0$ based on one or more historical treatment interventions;

performing the multi-factor survey of the injured individual at $T_1$ for the injury to obtain $T_1$ measurements associated with the predetermined set of factors, wherein the $T_1$ measurements include biologic measurements and functional metrics of the injured individual at $T_1$, wherein performing the multi-factor survey at $T_1$ comprises at least using the one or more diagnostic testing equipments on the injured individual to obtain at least a portion of the biologic measurements and functional metrics of the injured individual at $T_1$;

determining, by the computing device, a recovery score index for the injured individual at $T_1$ according to the predetermined technique reducing $T_1$ scalar values associated with the predetermined set of factors to a single representative value indicative of the injured individual's recovery status at $T_1$, wherein the $T_1$ scalar values correspond with at least a portion of the $T_1$ measurements obtained according to the one or more administrative rule sets;

if the recovery score index at $T_1$ is ≥1, then determining, by the computing device, a recovery phase classification at $T_1$;

calculating, by the computing device, a recovery score index delta based on the recovery score index at $T_1$ and the recovery score index at $T_0$;

calculating, by the computing device, a recovery velocity based on the recovery score index delta and time between $T_0$ and $T_1$, wherein the recovery velocity comprises the recovery score index delta divided by a time interval between $T_0$ and $T_1$, wherein calculating the recovery velocity comprises standardizing the recovery velocity, according to the one or more administrative rule sets for the injury sustained by the injured individual, by extrapolating the recovery score index at $T_1$ and the recovery score index at $T_0$ to identify a trajectory for a period of time mandated by the one or more administrative rule sets;

based on the recovery velocity and the recovery phase classification at $T_1$, determining by the computing device a date of maximum medical improvement for the injured individual, wherein the maximum medical improvement date comprises one of a past, a present and a future date and as based on a recovery velocity delta change of 10% to validate an active recovery;

causing to display the date of maximum medical improvement for the injured individual.

2. The method of claim 1, wherein the time between $T_0$ and $T_1$ is dependent upon the one or more administrative rule sets for the injury.

3. The method of claim 1, wherein each of determining the recovery phase classification at $T_0$ and determining the recovery phase classification at $T_1$ comprises determining whether available treatment options for the injury have been exhausted.

4. The method of claim 3, wherein the available treatment options comprise one or more of medications, therapies, diagnostic testing, and specialty consulting.

5. The method of claim 3, wherein the available treatment options are classified according to four stages.

6. The method of claim 1, wherein if the recovery velocity is one of positive and neutral and available treatment options have been exhausted, then the maximum medical improvement date is $T_0$.

7. The method of claim 1, wherein if the recovery velocity is one of positive and neutral and available treatment options have not been exhausted, then treatment is continued according to the one or more administrative rule sets and recovery phase classification is determined at $T_N$.

8. The method of claim 1, wherein the recovery velocity is ≤−0.167 RSID/week.

9. The method of claim 8, wherein if the available treatment options have been exhausted, then the maximum medical improvement date is $T_0$.

10. The method of claim 1, wherein if the recovery velocity is ≤−0.167 RSID/week, then treatment is continued according to the one or more administrative rule sets and recovery phase classification is determined at $T_N$.

11. The method of claim 1, wherein if the recovery velocity is ≥−0.167 RSID/week and available treatment options have not been exhausted, then treatment is continued according to the one or more administrative rule sets and recovery phase classification is determined at $T_N$.

12. The method of claim 1, wherein the measured set of factors comprise data measurements, and measuring the set of factors comprises performing diagnostic testing to obtain discrete data points.

13. A method of determining a rate of recovery for an injury comprising:
  performing a multi-factor survey of an injured individual at $T_0$ for an injury sustained by the injured individual to obtain $T_0$ measurements associated with a predetermined set of factors, wherein the $T_0$ measurements include biologic measurements and functional metrics of the injured individual at $T_0$, wherein performing the multi-factor survey at $T_0$ comprises at least using one or more diagnostic testing equipments on the injured individual to obtain at least a portion of the biologic measurements and functional metrics of the injured individual at $T_0$;
  determining, by a computing device, a recovery score index for the injured individual at $T_0$ according to a predetermined technique reducing $T_0$ scalar values associated with the predetermined set of factors to a single representative value indicative of the injured individual's recovery status at $T_0$, wherein the $T_0$ scalar values correspond with at least a portion of the $T_0$ measurements obtained according to one or more administrative rule sets, wherein the predetermined technique includes applying one or more statistical methods to one or more sets of scalar values that correspond with measurements obtained according to the one or more administrative rule sets;
  performing the multi-factor survey of the injured individual at $T_N$ for the injury to obtain $T_N$ measurements associated with the predetermined set of factors, wherein the $T_N$ measurements include biologic measurements and functional metrics of the injured individual at $T_N$, wherein performing the multi-factor survey at $T_N$ comprises at least using the one or more diagnostic testing equipments on the injured individual to obtain at least a portion of the biologic measurements and functional metrics of the injured individual at $T_N$;
  determining, by the computing device, a recovery score index for the injured individual at $T_N$ according to the predetermined technique reducing $T_N$ scalar values associated with the predetermined set of factors to a single representative value indicative of the injured individual's recovery status at $T_N$, wherein the $T_N$ scalar values correspond with at least a portion of the $T_N$ measurements according to the one or more administrative rule sets;
  based on the recovery score index at $T_N$ and the recovery score index at $T_0$ and the time between $T_0$ and $T_N$, generating by the computing device a rate of recovery for the injury sustained by the injured individual, wherein the rate of recovery comprises a recovery score index delta divided by the time interval between $T_0$ and $T_N$, wherein the rate of recovery is standardized based the on one or more administrative rule sets for the injury by extrapolating the recovery score index at $T_1$ and the recovery score index at $T_0$ to identify a trajectory for a period of time mandated by the one or more administrative rule sets, and wherein the rate of recovery is one of positive, neutral, and negative indicating that the individual is one of worsening, recovery is static and the individual is improving;
  causing to display the rate of recovery for the injury sustained by the injured individual.

14. The method of claim 13, wherein the time between $T_0$ and $T_N$ is dependent upon the one or more administrative rule sets for the injury.

15. A system for determining a maximum medical improvement and dating assignment for an injury, the system comprising:
  means for performing a multi-factor survey of an injured individual to obtain a plurality of sets of measurements at a plurality of times, wherein each set of measurements of the plurality of sets of measurements is associated with a predetermined set of factors and includes biologic measurements and functional metrics of the injured individual at a particular time of the plurality of times;
  a maximum medical improvement calculator configured to:
    determine a first recovery score index and a second recovery score index,
      the first recovery score index determined according to a predetermined technique reducing $T_0$ scalar values associated with the predetermined set of factors to a single representative value indicative of the injured individual's recovery status at $T_0$,
      the $T_0$ scalar values correspond with at least a portion of a first set of measurements of the plurality of sets of measurements obtained according to one or more administrative rule sets, wherein the predetermined technique includes applying one or more statistical methods to one or more sets of scalar values that correspond with measurements obtained according to the one or more administrative rule sets,
      the second recovery score index determined according to the predetermined technique reducing $T_1$ scalar values associated with the predetermined set of factors to a single representative value indicative of the injured individual's recovery status at $T_1$,
      the $T_1$ scalar values correspond with at least a portion of a second set of measurements of the plurality of sets of measurements obtained according to the one or more administrative rule sets;
    determine a recovery velocity that is standardized according to the one or more administrative rule sets for an injury sustained by the injured individual by extrapolating the first and second recovery score indexes to identify a trajectory for a period of time mandated by the one or more administrative rule sets; and
    generate and cause to display a maximum medical improvement date based on the recovery velocity and a recovery phase classification, wherein the maximum medical improvement date comprises one of a past, a present and a future date and as based on a recovery velocity delta change of 10% to validate an active recovery.

16. The system of claim 15, wherein each of the first and second recovery score indexes is based on a scale from 1 to 10.

17. The system of claim 15, wherein the first and second recovery score indexes are associated with time $T_0$ and time $T_1$, respectively.

18. The system of claim 17, wherein the time between $T_0$ and $T_1$ is dependent upon the one or more administrative rule sets for the injury.

19. The system of claim 15, wherein the recovery phase classification comprises one or more available treatment options for the injury.

20. The system of claim 19, wherein the one or more available treatment options comprise one or more of medications, therapies, diagnostic testing, and specialty consulting.

21. The system of claim 19, wherein the one or more available treatment options are classified according to four stages.

22. The system of claim 15, wherein the maximum medical improvement calculator determines whether available treatment options have been exhausted.

* * * * *